United States Patent [19]

Wu et al.

[11] Patent Number: 5,466,707
[45] Date of Patent: Nov. 14, 1995

[54] DIMERCAPTO-1,3-DITHIOLO-2-ONE OR THIONE MALEIMIDES, COMPOSITIONS CONTAINING THEM AND THEIR USE AS ANTIMICROBIAL AND MARINE ANTIFOULING AGENTS

[75] Inventors: Weishi W. Wu; Ravi B. Shankar; Duane R. Romer; R. Garth Pews, all of Midland, Mich.

[73] Assignee: The Dow Chemical Company, Midland, Mich.

[21] Appl. No.: 360,490

[22] Filed: Dec. 21, 1994

[51] Int. Cl.6 .......................... A01N 43/72; C07D 513/14
[52] U.S. Cl. ............................................. 514/411; 548/431
[58] Field of Search ............................. 514/411; 548/431

[56] References Cited

PUBLICATIONS

Hansen, T. K. et al., "Novel Maleimide–type Acceptors Based on Annelated 1,4–Dithiins," J. Chem. Soc. Perkin Trans. I, 1992, pp. 1807–1810.

*Primary Examiner*—Jacqueline Haley
*Attorney, Agent, or Firm*—S. Preston Jones; James M. Pelton

[57] ABSTRACT

Various 4,5-dimercapto-1,3-dithiolo-2-one or thione maleimides corresponding to the formula

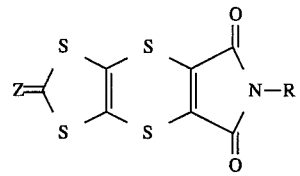

wherein R represents —H, phenyl, benzyl, phenethyl, a $C_1$–$C_{10}$ straight or branched chain alkyl radical, a $C_3$–$C_{10}$ cycloalkyl radical, a $C_1$–$C_{10}$ straight or branched chain alkoxy radical, a $C_3$–$C_{10}$ cycloalkoxy, an ester of the formula —$CH_2CH_2O$—$C(O)$—$R^1$, wherein $R^1$ represents a $C_1$–$C_5$ straight or branched chain alkyl radical or a $C_3$–$C_5$ cycloalkyl radical and Z represents oxygen or sulfur are disclosed.

These compounds have been found to exhibit antimicrobial and marine antifouling activity in industrial and commercial applications and compositions containing these compounds are so employed.

24 Claims, No Drawings

DIMERCAPTO-1,3-DITHIOLO-2-ONE OR THIONE MALEIMIDES, COMPOSITIONS CONTAINING THEM AND THEIR USE AS ANTIMICROBIAL AND MARINE ANTIFOULING AGENTS

FIELD OF THE INVENTION

The present invention is directed to certain 4,5-dimercapto-1,3-dithiolo-2-one or thione maleimides, compositions containing these type of compounds and their use as antimicrobial and marine antifouling agents.

BACKGROUND OF THE INVENTION

Hansen et al., J. Chem. Soc., Perkin Trans I, (1992), pages 1807–1810 teach various 4,5-dimethyl-1,3-dithiolo-2-one (or thione) maleimides corresponding to the formula

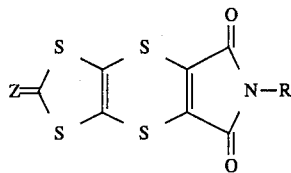

wherein R represents —H, substituted phenyl, benzyl, or a $C_1$–$C_2$ or $C_6$ alkyl radical and Z represents oxygen or sulfur. These compounds are taught as having "electron-acceptor" type behavior.

SUMMARY OF THE INVENTION

The present invention is directed to the antimicrobial and marine antifouling uses of 4,5-dimercapto-1,3-dithiolo-2-one or thione maleimides corresponding to the formula

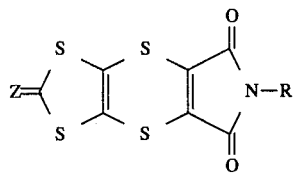

I wherein R represents —H, phenyl, benzyl, phenethyl, a $C_1$–$C_{10}$ straight or branched chain alkyl radical, a $C_3$–$C_{10}$ cycloalkyl radical, a $C_1$–$C_{10}$ straight or branched chain alkoxy radical, a $C_3$–$C_{10}$ cycloalkoxy, an ester of the formula —$CH_2CH_2O$—$C(O)$—$R^1$, wherein $R^1$ represents a $C_1$–$C_5$ straight or branched chain alkyl radical or a $C_3$–$C_5$ cycloalkyl radical and Z represents oxygen or sulfur.

The present invention is also directed to novel 4,5-dimercapto-1,3-dithiolo-2-one or thione maleimides corresponding to the formula

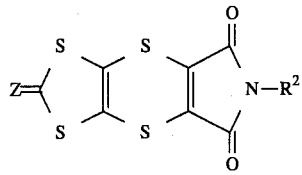

II wherein $R^2$ represents $C_3$–$C_{10}$ cycloalkyl, $C_1$–$C_{10}$ straight or branched chain alkoxy, $C_3$–$C_{10}$ cycloalkoxy, an ester of the formula —$CH_2CH_2O$—$C(O)$—$R^1$, wherein $R^1$ represents a $C_1$–$C_5$ straight or branched chain alkyl or $C_3$–$C_5$ cycloalkyl and Z represents oxygen or sulfur.

The present invention is further directed to a method for inhibiting microorganisms present in a microbial habitat which comprises contacting said microbial habitat with an antimicrobial composition comprising an inert diluent in admixture with an antimicrobially-effective amount of a compound corresponding to Formula I.

The antimicrobial compositions of the present invention can also be employed to treat surfaces exposed to a marine environment in which marine organisms grow to prevent the growth of said marine organisms on said surfaces.

DETAILED DESCRIPTION OF THE INVENTION

In the present specification and claims, the term "alkali metal" is employed to designate sodium, potassium, lithium or cesium.

In the present specification and claims, the term "halo" is employed to designate bromo, chloro, fluoro or iodo.

The maleimide compounds corresponding to Formula I of the present invention wherein Z is S can be prepared employing various preparative procedures such as those set forth below. In the following process schematic formulas, certain specific alkali metals, halo groups, specific solvents and the like are set forth. These representations are only presented for convenience and are not to be considered as an indication that these specifically representations are the only groups or materials which can be employed. Method A: In this procedure, an alkali metal dithiolate, conveniently prepared by adding, with stirring and under a nitrogen atmosphere, an alkali metal ethoxide to a suspension of finely powdered 4,5-bis(benzoylthio)-1,3-dithiole-2-thione in absolute ethanol. After a reaction period of about 30 minutes or so, the reaction mixture is mixed with anhydrous ether and upon standing, the alkali metal dithiolate product precipitates and is recovered for use in the present process. Stoichiometric amounts of the alkali metal dithiolate and an appropriately substituted 3,4-dichloromaleimide are mixed with a polar aprotic solvent, such as, for example, dimethylsulfoxide, N-methyl pyrrolidine, dry dimethylformamide or the like, and the mixture is stirred at room temperature under nitrogen for from about 0.5 to about 10 hours or more. In most cases the product precipitates out from the reaction mixture, if not, methanol and/or water can be added to aid in precipitation. The product is recovered by filtration, washed with water or methanol and air dried. The reaction scheme is as follows:

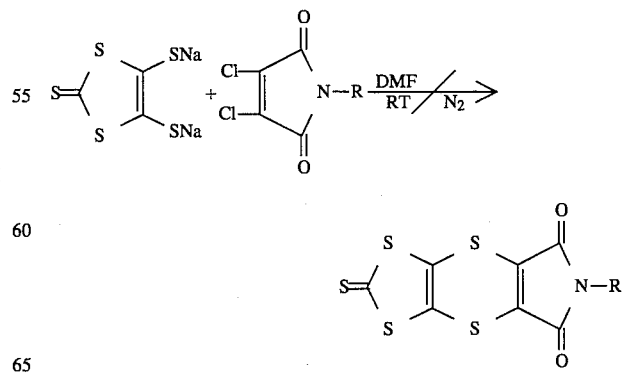

Method B: In this procedure, stoichiometric amounts of an alkali metal dithiolate, prepared as above in Method A, and an appropriate 3,4-dihalomaleimide such as 3,4-dichloromaleimide are mixed with a $C_1$–$C_8$-alkanol such as methanol, ethanol, isopropanol, butanol and the like. The mixture is stirred at room temperature under nitrogen for about 16 hours or more. Water is slowly added to precipitate the product, which after recovery by filtration, is washed with water, air dried and recrystallized from an alkanol such as methanol or ethanol. The reaction scheme is as follows:

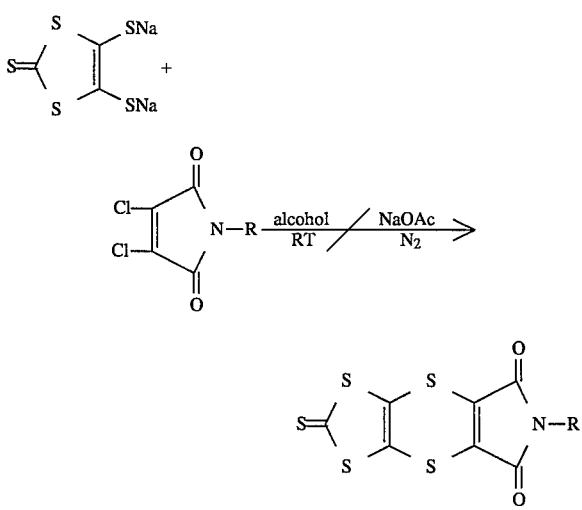

Method C: bis(tetraethylammonium) bis-(2-thioxo-1,3-dithiole-4,5-dithiolate)zinc(II) is reacted at room temperature with a slight excess of an appropriate 3,4-dihalomaleimide, preferably 3,4-dichloromaleimide, in the presence of a solvent such as tetrahydrofuran (THF) or an ether such as methyl ether, diethyl ether or glyme. The reaction scheme is as follows:

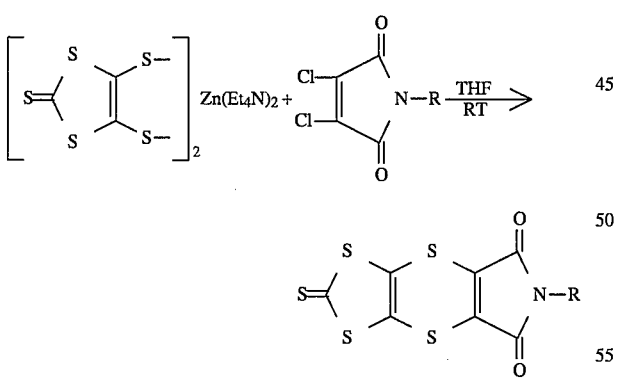

Method D: bis(tetraethylammonium) bis-(2-thioxo-1,3-dithiole-4,5-dithiolate)zinc(II) is reacted at room temperature with an appropriate 3,4-dichloromaleimide in the presence of a solvent such as acetone or methylisobutylketone for a period of from about 2 to about 3 days. The product normally precipitates out during the course of the reaction. Part of the acetone is evaporated off and the product is recovered by filtration followed by water washing and then air drying. The reaction scheme is as follows:

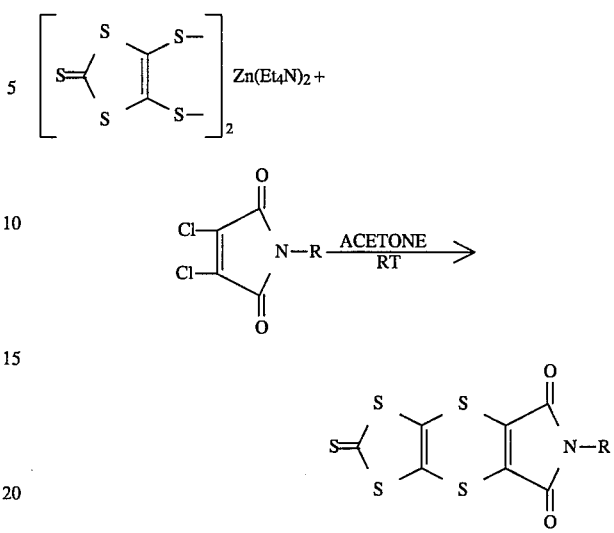

The maleimide compounds corresponding to Formula I of the present invention wherein Z is O can be prepared by oxidizing the above prepared thioxo compounds with from a slight excess to about a threefold excess of mercuric acetate. In carrying out this reaction, a mixture of the thioxo compound and mercuric acetate in a mixed solvent composed of a chlorine containing solvent such as, for example, but not limited to, chloroform, ethylene chloride, methylene chloride and hexachloroethane in admixture with acetic acid is reacted under reflux conditions for from about 1 to about 24 hours or more. The reaction product is filtered to remove insoluble mercury salts and the filtrate concentrated under reduced pressure to remove most of the solvent. The residue is redissolved in chloroform, washed first with aqueous potassium carbonate and then with water. The organic phase is separated and dried over magnesium sulfate. The product is then recovered by removal of the solvent under vacuum. Alternatively, after the filtration step, the filtrate is brought to dryness under vacuum followed by a thorough washing with water and then air drying to obtain the desired product.

The invention is further illustrated by the following examples:

EXAMPLE I: Preparation of 6-(1-Methylethyl)-2-thioxo-5H-1,3-dithiolo-(5,6)(1,4)dithiino(2,3-C)-pyrrole-5,7(6H)-dione

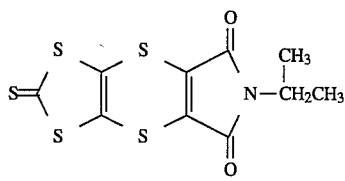

Following the procedure outlined as Method C, a reaction mixture was prepared by slowly adding 3.10 g (0.00390 mol) of bis(tetraethylammonium)-bis(2-thioxo-1,3-dithiolo-4,5-dithiolate Zn(II) to a solution of 1.60 g (0.00770 mol) of N-isopropyl-3,4-dichloromaleimide in 100 mL of tetrahydrofuran. The solution was stirred overnight (about 16 hours) at room temperature. To this solution was added 200 mL of water dropwise over a 1 hour period and the brown precipitate which resulted was filtered off, washed with water and dried over anhydrous sodium sulfate. The product was dissolved in hot ethanol and allowed to slowly recrystallize at room temperature for 1 hour, and then in a refrigerator for 72 hours. The crystalline product was filtered off and air dried. The product was recovered in a yield of 1.76 g (69 percent of theoretical) as green/brown crystals which melted at 135°–136° C.

EXAMPLE II: Preparation of 2-Thioxo-5H-1,3-dithiolo-(5,6)(1,4)dithiino(2,3-C)pyrrole-5,7-(6H)dione

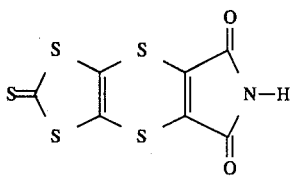

Following the procedure outlined as Method A, 0.83 g (5.0 mmol of 3,4-dichloromaleimide and 2.03 g (5.0 mmol) of sodium dithiolate were reacted at room temperature for 4 hours giving 0.65 g (45 percent of theoretical) of the title compound as a red-brown powder which melted at 219°–221° C./dec. MS (EI) m/z 291 (M$^+$), 247, 215, 172, $C_7HNO_2S_5$ requires 291; $^1$H NMR (DMSO-$d_6$) δ 11.6 (1H, s, NH); $^{13}$C NMR (DMSO-$d_6$) δ 212.34, 164.40, 135.62, 123.26.

Following the procedure outlined as Method C, 0.83 g (5.0 mmol) of 3,4-dichloromaleimide and 1.79 g (2.5 mmol) of bis(tetraethylammonium)-bis-(2-thioxo-1,3-dithiole-4,5-dithiolato) zinc(II) were reacted at room temperature for 1 hour giving 1.30 g (95 percent of theoretical) of the title compound as a red-brown powder purification by recrystallization from ethanol gave 1.19 g (87 percent of theoretical) of the product as red-brown needles melting at 221°–223° C.(dec); other analytical data were consistent with the data obtained above where Method A was employed.

EXAMPLE III: Preparation of 6-Methyl-2-thioxo-5H-1,3-dithiolo-(5,6)(1,4)dithiino(2,3-C)pyrrole-5,7(6H)-dione

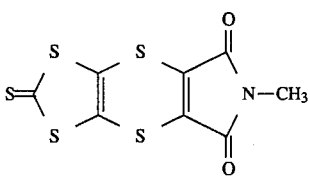

Following the procedure outlined as Method A, 0.50 g (2.8 mmol) of 3,4-dichloro-N-methylmaleimide and 1.15 g (2.8 mmol) of sodium dithiolate were reacted at room temperature for 4 hours giving 0.82 g (95 percent of theoretical) of the title compound as a yellow-brown powder which melted at 110–114° C. MS (EI) m/z 305 (M$^+$), 282, 215, 197, 140, 112, $C_8H_3NO_2S_5$ requires 305; $_1$H NMR (pyridine-$d_5$) δ 5.19 (3H,s, CH$_3$).

EXAMPLE IV: Preparation of 6-Ethyl-2-thioxo-5H-1,3-dithiolo-(5,6)(1,4)dithiino(2,3-C)pyrrole-5,7(6H)-dione

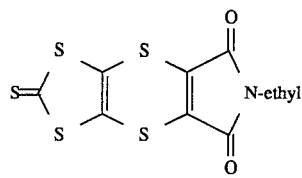

Following the procedure outlined as Method C, the title compound was recovered as a dark brown solid in a yield of 47 percent of theoretical melting at 143°–145° C.

EXAMPLE V: Preparation of 6-(2-(Acetyloxy)ethyl)-2-thioxo-5H-1,3-dithiolo-(5,6)(1,4)-dithiino(2,3-C)pyrrole-5,7(6H)-dione

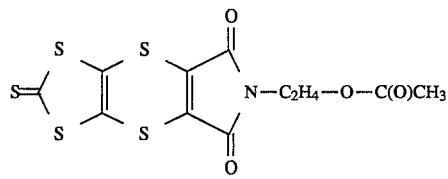

Following the procedure outlined as Method A, 0.70 g (2.8 mmol) of 3,4-dichloromethylmaleimide-N-ethyl acetate and 1.15 g (2.8 mmol) of sodium dithiolate were reacted at room temperature for 6 hours. At the end of the reaction period, most of the solvent was removed, under vacuum and the residue was diluted with 100 mL of methylene chloride, washed twice with 30 mL portions of 5 percent aqueous HCl and then washed with 30 mL of water. The organic phase was dried over anhydrous magnesium sulfate and the solvent evaporated off under vacuum giving 0.82 g (78 percent of theoretical) of the title compound as a thick brown oil, which solidified on standing at room temperature and melted at 103°–106° C. MS (EI)m/z 377 (M$^+$), 317, 291, 198, $C_{11}H_7NO_4S_5$ requires 377; $^1$H NMR (CDCl$_3$-$d_5$) δ 4.22 (2H, t, CH$_2$CH$_2$), 3.82, (2H, t, CH$_2$CH$_2$), 2.04 (3H, s, CH$_3$); $^{13}$C NMR (CDCl$_3$-$d_5$) δ 209.31, 170.79, 163.08, 135.31, 120.93, 61.26, 38.93, 20.81.

EXAMPLE VI: Preparation of 6-Ethoxy-2-thioxo-5H-1,3-dithiolo-(5,6)(1,4)dithiino(2,3-C)pyrrole-5,7(6H)-dione

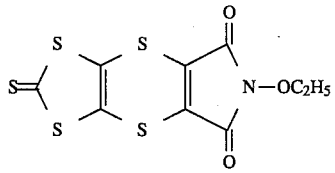

Following the procedure outlined as Method A, 0.58 g (2.8 mmol) of 3,4-dichloro-N-ethoxymaleimide and 1.15 g (2.8 mmol) of sodium dithiolate were reacted at room temperature for 4 hours giving 0.82 g (95 percent of theoretical) of the title compound as a yellow-brown powder which melted at 171°–173° C./dec. MS (EI) m/z 335 (M$^+$), 291,263, 231, $C_9H_5NO_3S_5$ requires 335; $^1$H NMR (DMSO-$d_6$) δ 4.09 (2H, q, CH$_2$CH$_3$), 1.24 (3H, t, CH$_2$C$\underline{H}_3$); $^{13}$C NMR (DMSO-$d_6$) δ 2$\overline{13}$.60, 159.60, 133.73, 124.31, 73.73, 13.42.

EXAMPLE VII: Preparation of 6-n-Propyl-2-thioxo-5H-1,3-dithiolo-(5,6)(1,4) dithiino(2,3-C)pyrrole-5,7(6H)-dione

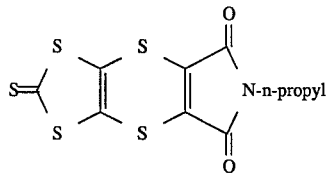

Following the procedure outlined as Method C, 1.30 g (5.0 mmol) of 3,4-dichloro-N-n-propylmaleimide and 1.79 g (2.5 mmol) of b is(tetraethylammonium)-bis-(2-thioxo-1, 3-dithiole-4,5-d ithiolato) zinc(II) were reacted at room temperature for 8 hours giving 1.54 g (93 percent of theoretical of the title compound as a brown powder which after recrystallization from ethanol gave 1.43 g (86 percent of theoretical) of the purified compound as brown needles melting at 104°–106° C. MS (EI) m/z 333 (M$^+$), 289, 257,248, 215, 172, $C_{10}H_7NO_2S_5$ requires 33; $^1$H NMR (CDCl$_3$) δ 3.38 (2H, t, C$\underline{H_2}$CH$_2$CH$_3$ ), 1.52 (2H, m, CH$_2$C$\underline{H_2}$CH$_3$), 0.84 (3H, t, CH$_2$C$\overline{H_2}$CH$_3$); $^{13}$C NMR (CDCl$_3$) δ 212.90, 163.58, 135.52, 123.69, $\overline{40.98}$, 21.26, 11.10.

EXAMPLE VIII: Preparation of 6-n-Butyl-2-thioxo-5H-1,3-dithiolo-(5,6)(1,4) dithiino(2,3-C)-pyrrole-5,7(6H)-dione

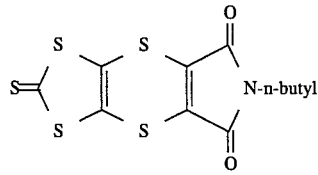

Following the procedure outlined as Method C, 3,4-dichloro-N-n-butylmaleimide and bis(tetraethyl-ammonium)bis-(2-thioxo-1,3-dithiole-4,5-dithiolato) zinc(II) were reacted to give the title compound as a dark brown amorphous solid in a yield of 75 percent of theoretical. MS (EI) mz 347 (M$^+$).

EXAMPLE IX: Preparation of 6-(1-Methylpropyl)-2-thioxo-5H-1,3-dithiolo-(5,6)(1,4) dithiino(2,3-C )-pyrrole-5,7(6H)-dione

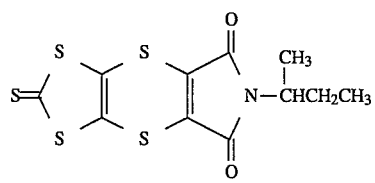

Following the procedure outlined as Method C, the title compound was recovered as an orange-brown powder in a yield of 77 percent of theoretical, melting at 238°–240° C./dec.

EXAMPLE X: Preparation of 6-n-Hexyl-2-thioxo-5H-1,3-dithiolo-(5,6)(1,4)dithiino (2,3-C)pyrrole-5,7(6H )-dione

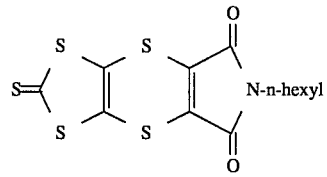

Following the procedure outlined as Method C, the title compound was recovered as a black amorphous solid in a yield of 98 percent of theoretical. MS (EI) m/z 377 (M$^+$2, 20), 375 (M$^+$81) 88 (100); $^1$H NMR (DMSO) δ 3.62 (2H, m), 1.62 (2H, m), 1.45 (2H, m), 128 (bs, 4H), 0.86 (bs, 3H).

EXAMPLE XI: Preparation of 6-Cyclohexyl-2-thioxo-5H-1,3-dithiolo-(5,6)(1,4) dithiino(2,3-C)-pyrrole-5,7(6H)-dione

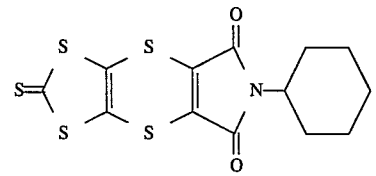

Following the procedure outlined as Method C, the title compound was recovered as a green powder in a yield of 95 percent of theoretical. MS (EI) m/z 373 (M$^+$, 51), 388 (100).

EXAMPLE XII: Preparation of 6-n-decyl-2-thioxo-5H-1,3-dithiolo-(5,6)(1,4)dithiino (2,3-C)pyrrole-5,7(6H)-dione

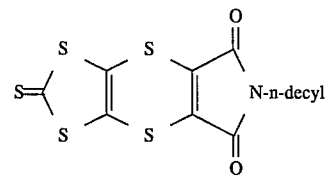

Following the procedure outlined as Method C, the title compound was recovered as a black amorphous solid in a yield of 94 percent of theoretical. MS (EI) m/z 433 (M$^+$2,9) 431 (M$^+$25) 88 (100); $^1$H NMR (DMSO) δ 4.04 (2H, m), 1.23–1.15 (bm, 16H), (1H, d), 6.93 (1H, s), 6.92 (1H,d), 3.76 (3H, s); 0.85 (bs, 3H).

EXAMPLE XIII: Preparation of 6-Phenyl-2-thioxo-5H-1,3-dithiolo-(5,6)(1,4)dithiino (2,3-C)-pyrrole-5,7(6H)-dione

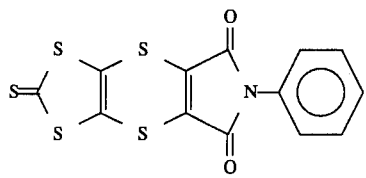

Following the procedure outlined as Method C, 1.20 g (5.0 mmol) of 3,4-dichloro-N-phenylmaleimide and 1.79 g (2.5 mmol) of bis(tetraethylammonium)bis-(2-thioxo-1,3-dithiole-4,5-dithiolato) zinc(II) were reacted at room temperature for 6 hours to give 1.72 g (94 percent of (theoretical) of the title compound as a green-yellow powder which after recrystallization from ethanol gave 1.61 g (88 percent of theoretical) of the desired compound as green-yellow needles melting at 231°–233° C./dec. MS (EI) m/z 367 (M$^+$), 369, 323, 291, 248, 159, 119, $C_{13}H_5NO_2S_5$ requires 367; $^1$H NMR (DMSO-d$_6$) δ 7.50 (2H, t), 7.44 (1H, M), 7.34 (2H, t); $^{13}$C NMR (DMSO-d$_6$) δ 213.00, 162.53, 135.00, 131.18, 129.05, 128.37, 126.85, 123.76.

EXAMPLE XIV: Preparation of 6-Benzyl-2-thioxo-5H-1,3-dithiolo-(5,6)(1,4) dithiino(2,3-C)pyrrole-5,7(6H)-dione

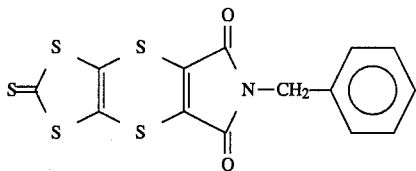

Following the procedure outlined as Method C, the title compound was recovered as a reddish-brown solid in a yield of 98 percent of theoretical melting at 174°–176° C./dec. MS (EI)m/z 383 (M$^+$2, 25), 381, (M$^+$, 100).

EXAMPLE XV: Preparation of 6-Phenethyl-2-thioxo-5H-1,3-dithiolo-(5,6)(1,4) dithiino(2,3-C)pyrrole-5,7(6H)-dione

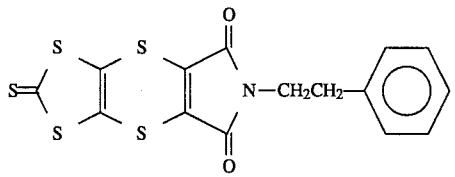

Following the procedure outlined as Method C, the title compound was recovered as a reddish-brown solid in a yield of 88 percent of theoretical melting at 162°–163° C./dec. MS (EI)m/z 397 (M$^+$2, 24), 395, (M$^+$, 100).

EXAMPLE XVI: Preparation of 6-(3-Methoxyphenyl)-2-thioxo-5H-1,3-dithiolo-(5,6)(1,4)-dithiino(2,3-C)pyrrole-5,7(6H)-dione

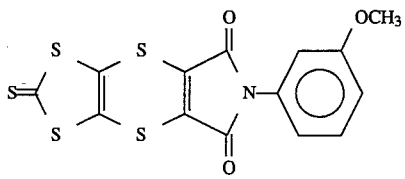

Following the procedure outlined as Method A, 0.75 g (2.8 mmol) of 3,4-dichloro-N-(3-methoxyphenyl)-maleimide and 1.15 g (2.8 mmol) of sodium dithiolate were reacted at room temperature for 30 minutes to give 0.67 g (60 percent of theoretical) of the title compound as a green-yellow powder melting at 211°–213° C./dec. MS (EI) m/z 397 (M$^+$), 353, 321, 277, 248, 189, 149, $C_{14}H_7NO_3S_5$ requires 397; $^1$H NMR (DMSO-d$_6$) δ 7.41 (1H, t), 7.01 (1H, d), 6.93 (1H, s), 6.92 (1H,d), 3.76 (3H, s); $^{13}$C NMR (DMSO-d$_6$) δ 212.81, 207.82, 162.21, 159.21, 135.87, 131.98, 129.66, 123.69, 118.93, 113.79, 112.67.

EXAMPLE XVII: Preparation of 6-(4-Fluorophenyl)-2-thioxo-5H-1,3-dithiolo-(5,6)(1,4)-dithiino (2,3-C)pyrrole-5,7(6H )-dione

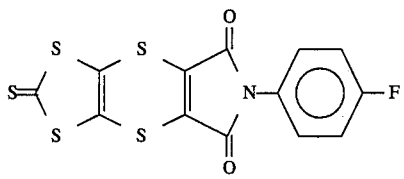

Following the procedure outlined as Method A, 0.75 g (2.8 mmol) of 3,4-dichloro-N-(4-fluorophenyl)-maleimide and 1.15 g (2.8 mmol) of sodium dithiolate were reacted at room temperature for 2 hours to give 0.74 g (69 percent of theoretical) of the title compound as a green-yellow powder melting at 234°–236° C./dec. MS (EI) m/z 385 (M$^+$), 341, 309, 265, 248, 199, 177, 137.

EXAMPLE XVIII: Preparation of 2-Oxo-5H-1,3-dithiolo-(5,6)(1,4)dithiino (2,3-C)pyrrole-5,7-(6H)-dione

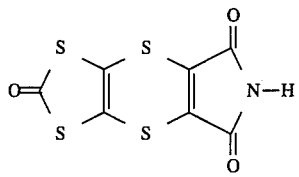

A mixture of 0.24 g (0.81 mmol of 2-thioxo-5-1,3-dithiolo-(5,6)(1,4)dithiino(2,3-C)pyrrole-5,7-(6H)-dione and 0.50 g (1.57 mmol) of mercuric acetate in 70 mL of chloroform and 25 mL of acetic acid were reacted at room temperature for 6 hours giving 0.17 g (78 percent of theoretical) of the title compound as a brown powder which melted at 229°–232° C. MS (EI) m/z 275 (M$^+$), 247, 202,

171.

EXAMPLE XIX: Preparation of 6-Phenyl-2-oxo-5H-1,3-dithiolo-(5,6)(1,4)dithiino(2,3-C)pyrrole-5,7(6H)-dione

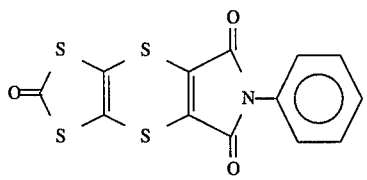

A mixture of 0.55 g (1.15 mmol of 6-Phenyl-2-thioxo-5H-1,3-dithiolo-(5,6)(1,4)dithiino(2,3-C)-(pyrrole-5,7-6H)-dione and 1.43 g (4.5 mmol) of mercuric acetate in 200 mL of chloroform and 80 mL of acetic acid were reacted at room temperature for 6 hours giving 0.42 g (84 percent of theoretical) of the title compound as shining purple-brown flakes which melted at 203°–207° C. MS (EI) m/z 51 ($M^+$), 324, 279, 247, 219, 171, 159, 119, $C_{13}H_5NO_3S_4$ requires 351; $^1H$ NMR (DMSO-$d_6$) δ 7.49 (2H, q), 7.43 (1H, q), 7.35 (2H, d); $^{13}C$ NMR (DMSO-$d_6$) δ 190.44, 162.46, 135.33, 131.13, 128.96, 128.27, 126.78, 113.51.

EXAMPLE XX: Preparation of 6-(1-Methylpropyl)-2-oxo-5H-1,3-dithiolo-(5,6)(1,4)dithiino(2,3-C)-pyrrole-5,7(6H)-dione

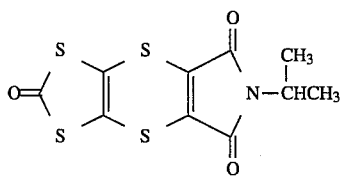

A mixture of 0.55 g (1.44 mmol of 6-(1-methyl-propyl)-2-thioxo-5H-1,3-dithiolo-(5,6)(1,4)dithiino-(2,3-C)-(pyrrole-5,7-6H)-dione and 1.38 g (4.32 mmol) of mercuric acetate in 200 mL of chloroform and 80 mL of acetic acid were reacted under reflux for 18 hours. The solution was filtered through Celite® and concentrated under vacuum. The residue was redissolved in chloroform, washed with a 10 percent sodium carbonate solution and then a saturated sodium chloride solution. After drying over sodium sulfate, the solution was concentrated under vacuum to give 0.36 g (75 percent of theoretical) of the title compound as an amorphous green solid.

EXAMPLE XXI: Preparation of 6-n-Butyl-2-oxo-5H-1,3-dithiolo-(5,6)(1,4)dithiino(2,3-C)pyrrole-5,7(6H)-dione

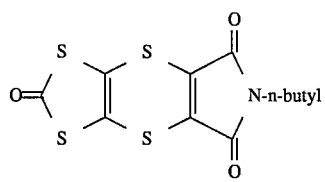

Following the procedure outlined for preparing the oxo compounds, a mixture of 6-n-butyl-2-thioxo-5H-1,3-dithiolo-(5,6)(1,4)dithiino(2,3-C)-pyrrole-5,7-(6H)-dione and mercuric acetate were reacted to give 2.16 g (57 percent of theoretical) of the title compound as a dark brown amorphous solid.

EXAMPLE XXII: Preparation of 6-(1-Methylethyl)-2-oxo-5H-1,3-dithiolo-(5,6)(1,4)dithiino(2,3-C)-pyrrole-5,7(6H)-dione

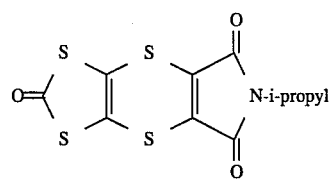

Following the procedure outlined for preparing the oxo compounds, a mixture of 6-i-propyl-2-thioxo-5H-1,3-dithiolo-(5,6)(1,4 )dithiino(2,3-C)-(pyrrole-5,7-(6H)-dione and mercuric acetate were reacted to give 0.36 g (75 percent of theoretical) of the title compound as dark green crystals which melted at 136–138° C.

EXAMPLE XXIII: Preparation of 6-Ethyl-2-oxo-5H-1,3-dithiolo-(5,6)(1,4)dithiino(2,3-C)-pyrrole-5,7(6H)-dione

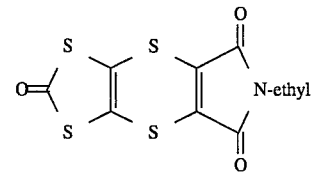

Following the procedure outlined for preparing the oxo compounds, a mixture of 6-ethyl-2-(thioxo-5H-1,3-dithiolo-(5,6)(1,4)dithiino(2,3-C)-(pyrrole-5,7-(6H)-dione and mercuric acetate were reacted to give 1.56 g(47 percent of theoretical) of the title compound as a dark brown solid which melted at 153–155° C.

EXAMPLE XXIV: Preparation of 6-n-Hexyl-2-oxo-5H-1,3-dithiolo-(5,6)(1,4)dithiino(2,3-C)-pyrrole-5,7(6H)-dione

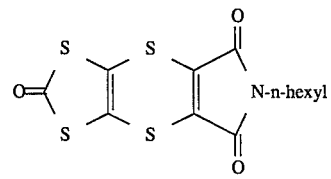

Following the procedure outlined for preparing the oxo compounds, a mixture of 6-n-hexyl-2-thioxo-5H-1,3-dithiolo-(5,6)(1,4) dithiino(2,3-C)-pyrrole-5,7-(6H)-dione and mercuric acetate were reacted to give 0.39 g (82 percent of theoretical) of the title compound as a dark brown waxy solid.

EXAMPLE XXV: Preparation of 6-n-Decyl;-2-oxo-5H-1,3-dithiolo-(5,6)(1,4)dithiino (2,3-C)pyrrole-5,7(6H)-dione

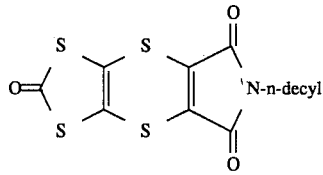

Following the procedure outlined for preparing the oxo compounds, a mixture of 6-n-decyl-2-thioxo-5H-1,3-dithiolo-(5,6)(1,4)dithiino(2,3-C)-(pyrrole-5,7-(6H)-dione and mercuric acetate were reacted to give 0.39 g (82 percent of theoretical) of the title compound as an amorphous dark brown solid.

EXAMPLE XXVI: Preparation of 6-Benzyl-2-oxo-5H-1,3-dithiolo-(5,6)(1,4)dithiino (2,3-C)-pyrrole-5,7(6H)-dione

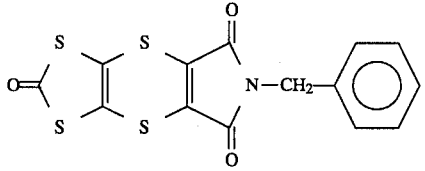

Following the procedure outlined for preparing the oxo compounds, a mixture of 6-benzyl-2-thioxo-5H-1,3-dithiolo-(5,6)(1,4)dithiino(2,3-C)-(pyrrole-5,7-(6H)-dione and mercuric acetate were reacted to give 0.32 g (67 percent of theoretical) of the title compound as a red-orange solid which melted at 167–170° C.

EXAMPLE XXVII: Preparation of 6-Phenethyl-2-oxo-5H-1,3-dithiolo-(5,6)(1,4)dithiino (2,3-C)-pyrrole-5,7(6H)-dione

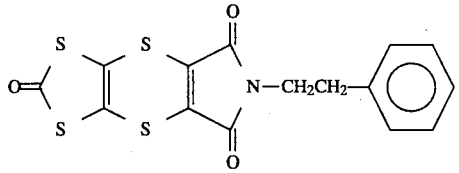

Following the procedure outlined for preparing the oxo compounds, a mixture of 6-phenyl-2-thioxo-5H-1,3-dithiolo-(5,6)(1,4)dithiino(2,3-C)-(pyrrole-5,7-(6H)-dione and mercuric acetate were reacted to give 0.44 g (89 percent of theoretical) of the title compound as a dark brown solid which melted at 173°–177° C.

EXAMPLE XXVIII: Preparation of 6-Cyclohexyl-2-oxo-5H-1,3-dithiolo-(5,6)(1,4) dithiino(2,3-C)-pyrrole-5,7(6H)-dione

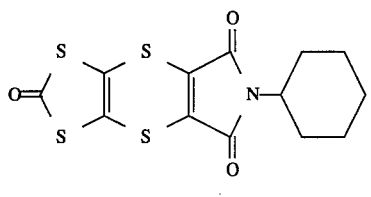

Following the procedure outlined for preparing the oxo compounds, a mixture of 6-cyclohexyl-2-thioxo-5H-1,3-dithiolo-(5,6)(1,4)dithiino(2,3-C)-(pyrrole-5,7-(6H)-dione and mercuric acetate were reacted to give 0.33 g (69 percent of theoretical) of the title compound as an amorphous solid.

Preparation of Starting Materials

EXAMPLE XXVIII: Preparation of Bis(tetraethylammonium)-bis(2-thioxo-1,3-dithiolo-4,5-dithiolate zinc(II)

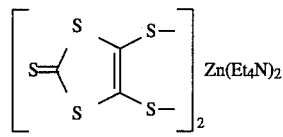

To a 3 liter three-necked round bottom flask, equipped with a mechanical stirrer and an addition funnel to which was connected a nitrogen gas line, was added 228 g (180 mL, 3.0 mol) of carbon disulfide. The temperature was brought to about 5° C. To this solution was added in one portion and under nitrogen, 23 g (0.1 mol) of sodium metal, which had been cut into small pieces and washed with hexane to remove mineral oil present from storage. After stirring the thus-formed suspension for 15 minutes, 150 mL of N,N-dimethylformamide was slowly added over a period of 4 hours. During this time, the solution turned from colorless to dark red. At the end of the addition, the cold bath was removed and the mixture was allowed to stir at room temperature for 20 hours. The mixture was cooled in an acetone-ice bath to about 5° C. and 150 mL of methanol was slowly added. After stirring for 15 minutes, an additional 350 mL of N,N-dimethylformamide was added followed by 750 mL of water. The red-colored solution was then carefully transferred to a 5 liter three-necked flask equipped with a mechanical stirrer and an addition funnel. To the stirred solution were added, 20 g (0.5 mol) of zinc chloride in 500 mL of about 28 percent ammonium hydroxide and 500 mL of methanol. A solution of 31 g (0.15 mol) of tetraethylammonium bromide in 250 mL of water was then added dropwise over a period of 1 hour and the mixture was stirred for an additional 24 hours at room temperature. The reaction mixture was filtered on a Bucher funnel and the product was recovered as red needles. The product was washed sequentially with 500 mL of water, 400 mL of isopropanol and 400 mL of ether. After air drying, the product was recovered in a yield of 43.6 g (48.6 percent of theoretical, based on sodium) and melted at 201–204° C.

|  | % C | % H | % N |
|---|---|---|---|
| Analysis: Calc. for $C_{22}H_{40}N_2S_{10}Zn$ | 36.77 | 5.61 | 3.90 |
| Found: | 36.62 | 5.19 | 3.81 |

Antimicrobial Activity

The compounds of this invention are useful as antimicrobial additives, and they can be added to industrial products such as paints, inks, adhesives, soaps, cutting oils, textiles, and paper and pigment slurries and to styrene-butadiene latexes used for paper coatings.

The compounds are also useful as antimicrobial additives in such personal care products as hand creams, lotions, shampoos, and hand soaps.

As appreciated in the art, not all of the compounds disclosed herein are active at the same concentrations or against the same microbial species. That is, there is some compound-to-compound variation in antimicrobial potency and spectrum of antimicrobial activity.

The present invention is also directed to a method for inhibiting microorganisms which comprises contacting said microorganisms or habitat thereof with an effective amount of the compounds of this invention.

The antimicrobial compounds of this invention may be added directly to aqueous formulations susceptible to microbial growth, either undiluted or dissolved in inert diluents such as organic solvents such as glycols, alcohols, or acetone. They may also be added alone or in combination with other preservatives.

As used herein, the term "microorganism" is meant to refer to bacteria, fungi, viruses, algae, subviral agents and protozoa.

As used herein, the term "antimicrobially-effective amount" refers to that amount of one or a mixture of two or more of the compounds, or of a composition comprising such compound or compounds, of this invention needed to exhibit inhibition of selected microorganisms. Typically, this amount varies from providing about 1 part per million (ppm) to about 5,000 ppm by weight of the compound to a microbial habitat being contacted with the compound. Such amounts vary depending upon the particular compound tested and microorganism treated. Also, the exact concentration of the compounds to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weight, of a microbial habitat.

The term "microbial habitat" refers to a place or type of site where a microorganism naturally or normally lives or grows. Typically, such a microbial habitat will be an area that comprises a moisture, nutrient, and/or an oxygen source such as, for example, a cooling water tower or an air washing system.

The terms "inhibition", "inhibit" or "inhibiting" refer to the suppression, stasis, kill, or any other interference with the normal life processes of microorganisms that is adverse to such microorganisms, so as to destroy or irreversibly inactivate existing microorganisms and/or prevent or control their future growth and reproduction.

The antimicrobial activity of the compounds of the present invention is demonstrated by the following techniques.

The antimicrobial activity of the compounds of the present invention is set forth as the minimum inhibitory concentration (MIC) for the active compounds and is determined for nine (9) bacteria, using nutrient agar, and seven (7) yeast and fungi, using malt yeast agar. This determination is conducted using a one percent solution of the test compound prepared in a mixture of acetone and water.

The nutrient agars are prepared by adding 23 g of nutrient agar to one-liter of deionized water. In addition, the alkaline medium is prepared by adjusting a 0.04 M solution of N-[tris-(hydroxymethyl)methyl]-glycine buffered deionized water with concentrated sodium hydroxide to a pH of 8.5.

Malt yeast agar is prepared by adding 3 g yeast extract and 45 g malt agar per liter of deionized water. The specific agar is dispensed in 30 mL aliquots into 25×200 mm test tubes, capped and autoclaved for 15 minutes at 115° C.

The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 250, 100, 50, 25, 10, 5, 2.5 1.0 and zero parts per million of the test compound in the agar, thus having a known concentration of test compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per mL of suspension of a particular bacteria. Aliquots of 0.3 mL of each of the bacterial suspensions are used to fill the individual wells of Steer's Replicator. For each microbial suspension, 0.3 mL was used to fill three wells (i.e., three wells of 0.3 mL each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 mL of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension to 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table I lists the bacteria, yeast and fungi used in the MIC test described above along with their respective American Type Culture Collection (ATCC) identification numbers.

TABLE I

Organisms used in the Minimum Inhibitory Concentration Test

| Organism | ATCC No. |
|---|---|
| Bacteria | |
| *Bacillus subtilis* (Bs) | 8473 |
| *Enterobacter aerogenes* (Ea) | 13048 |
| *Escherichia coli* (Ec) | 11229 |
| *Klebsiella pneumoniae* (Kp) | 8308 |
| *Proteus vulgaris* (Pv) | 881 |
| *Pseudomonas aeruginosa* (Pa) | 10145 |
| *Pseudomonas aeruginosa* (PRD-10) | 15442 |
| *Salmonella choleraesuis* (Sc) | 10708 |
| *Staphylococcus aureus* (Sa) | 6538 |
| Yeast/Fungi | |
| *Aspergillus niger* (An) | 16404 |

TABLE I-continued

Organisms used in the Minimum Inhibitory Concentration Test

| Organism | ATCC No. |
|---|---|
| *Candida albicans* (Ca) | 10231 |
| *Penicillium chrysogenum* (Pe) | 9480 |
| *Saccharomyces cerevisiae* (Sc) | 4105 |
| *Trichoderma viride* (Tv) | 8678 |
| *Aureobasidium pullulan* (Ap) | 16622 |
| *Fusarium oxysporum* (Fo) | 48112 |

In Tables II and III, the MIC values of the compounds of the present invention as compared to the MIC of a standard commercial preservative (with 1-(3-chloroallyl)-3,5,7-triaza-1-azoniaadamantane chloride as the active agent, and referred to in Tables II and III as "STANDARD") are set forth for the bacteria organisms and yeast/fungi organisms which are listed in Table I.

TABLE II

Minimum Inhibitory Concentrations for Test Compounds in Bacteria Species (in ppm)

| Compound (Example No.) | | Bs | Ea | Ec | Kp | Pv | PRD | Pa | Sc | Sa |
|---|---|---|---|---|---|---|---|---|---|---|
| STANDARD | pH 6.8 | <10 | 100 | 50 | 25 | 50 | >500 | >500 | 50 | 25 |
| | pH 8.2 | 250 | 500 | >500 | 500 | 500 | >500 | >500 | >500 | 500 |
| (I) | pH 6.8 | <10 | >500 | >500 | >500 | >500 | >500 | >500 | >500 | 50 |
| | pH 8.2 | 250 | >500 | >500 | >500 | >500 | >500 | >500 | >500 | 250 |
| (II) | pH 6.8 | 50 | 250 | 50 | 250 | 50 | 250 | 250 | 250 | 50 |
| | pH 8.2 | 250 | >500 | >500 | >500 | >500 | >500 | >500 | >500 | 100 |
| (III) | pH 6.8 | 50 | >500 | >500 | >500 | >500 | >500 | >500 | >500 | 250 |
| | pH 8.2 | >500 | >500 | >500 | 100 | >500 | >500 | >500 | >500 | >500 |
| (IV) | pH 6.8 | 100 | >500 | >500 | >500 | >500 | >500 | >500 | >500 | 250 |
| | pH 8.2 | 250 | >500 | >500 | >500 | >500 | >500 | >500 | >500 | 500 |
| (V) | pH 6.8 | 25 | >500 | 500 | 500 | 250 | >500 | >500 | >500 | 50 |
| | pH 8.2 | >500 | >500 | >500 | >500 | >500 | >500 | >500 | >500 | >500 |
| (VI) | pH 6.8 | 250 | >500 | >500 | >500 | >500 | >500 | >500 | >500 | 250 |
| | pH 8.2 | >500 | >500 | >500 | >500 | >500 | >500 | >500 | >500 | >500 |
| (VII) | pH 6.8 | <10 | >500 | >500 | >500 | 250 | >500 | >500 | >500 | 50 |
| | pH 8.2 | 100 | >500 | >500 | 100 | >500 | >500 | >500 | >500 | 100 |
| (VIII) | pH 6.8 | <10 | >500 | >500 | >500 | >500 | >500 | >500 | >500 | 25 |
| | pH 8.2 | 100 | >500 | >500 | >500 | >500 | >500 | >500 | >500 | 100 |
| (IX) | pH 6.8 | 100 | >500 | >500 | >500 | >500 | >500 | >500 | >500 | 100 |
| | pH 8.2 | >500 | >500 | >500 | >500 | >500 | >500 | >500 | >500 | 250 |
| (X) | pH 6.8 | <10 | >500 | >500 | >500 | >500 | >500 | >500 | >500 | <10 |
| | pH 8.2 | 25 | >500 | >500 | >500 | >500 | >500 | >500 | >500 | 100 |
| (XI) | pH 6.8 | 50 | >500 | >500 | >500 | >500 | >500 | >500 | >500 | 10 |
| | pH 8.2 | 500 | >500 | >500 | >500 | >500 | >500 | >500 | >500 | 500 |
| (XII) | pH 6.8 | 100 | >500 | >500 | >500 | >500 | >500 | >500 | >500 | >500 |
| | pH 8.2 | >500 | >500 | >500 | >500 | >500 | >500 | >500 | >500 | >500 |
| (XIII) | pH 6.8 | >500 | >500 | >500 | >500 | >500 | >500 | >500 | >500 | >500 |
| | pH 8.2 | >500 | >500 | >500 | >500 | >500 | >500 | >500 | >500 | >500 |
| (XIV) | pH 6.8 | 100 | >500 | >500 | >500 | >500 | >500 | >500 | >500 | 50 |
| | pH 8.2 | 250 | >500 | >500 | >500 | >500 | >500 | >500 | >500 | 250 |
| (XV) | pH 6.8 | >500 | >500 | >500 | >500 | >500 | >500 | >500 | >500 | >500 |
| | pH 8.2 | >500 | >500 | >500 | >500 | >500 | >500 | >500 | >500 | >500 |
| (XVI) | pH 6.8 | >500 | >500 | >500 | >500 | >500 | >500 | >500 | >500 | >500 |
| | pH 8.2 | >500 | >500 | >500 | >500 | >500 | >500 | >500 | >500 | >500 |
| (XVII) | pH 6.8 | >500 | >500 | >500 | >500 | >500 | >500 | >500 | >500 | >500 |
| | pH 8.2 | >500 | >500 | >500 | >500 | >500 | >500 | >500 | >500 | >500 |
| (XVIII) | pH 6.8 | <10 | 50 | 25 | 25 | 25 | 500 | 25 | 25 | <10 |
| | pH 8.2 | 25 | >500 | >500 | >500 | 250 | >500 | >500 | 100 | 25 |
| (XIX) | pH 6.8 | 500 | >500 | >500 | >500 | >500 | >500 | >500 | >500 | 50 |
| | pH 8.2 | 500 | >500 | >500 | 100 | >500 | >500 | >500 | >500 | 50 |
| (XX) | pH 6.8 | <10 | >500 | >500 | >500 | >500 | >500 | >500 | >500 | <10 |
| | pH 8.2 | 50 | >500 | >500 | >500 | >500 | >500 | >500 | >500 | 100 |
| (XXI) | pH 6.8 | 25 | >500 | >500 | >500 | 250 | >500 | >500 | >500 | 25 |
| | pH 8.2 | 250 | >500 | >500 | >500 | >500 | >500 | >500 | >500 | 250 |

TABLE II-continued

Minimum Inhibitory Concentrations for Test Compounds
in Bacteria Species (in ppm)

| Compound (Example No.) | | Bs | Ea | Ec | Kp | Pv | PRD | Pa | Sc | Sa |
|---|---|---|---|---|---|---|---|---|---|---|
| (XXII) | pH 6.8 | <10 | >500 | >500 | >500 | >500 | >500 | >500 | >500 | 25 |
|  | pH 8.2 | 50 | >500 | >500 | >500 | >500 | >500 | >500 | >500 | 50 |
| (XXIII) | pH 6.8 | 250 | >500 | >500 | >500 | >500 | >500 | >500 | >500 | 25 |
|  | pH 8.2 | >500 | >500 | >500 | >500 | >500 | >500 | >500 | >500 | 25 |
| (XXIV) | pH 6.8 | <10 | >500 | >500 | >500 | 500 | >500 | >500 | >500 | <10 |
|  | pH 8.2 | 50 | >500 | >500 | >500 | >500 | >500 | >500 | >500 | 100 |
| (XXV) | pH 6.8 | 25 | >500 | >500 | >500 | 500 | >500 | >500 | >500 | 50 |
|  | pH 8.2 | 50 | >500 | >500 | >500 | >500 | >500 | >500 | >500 | 25 |
| (XXVI) | pH 6.8 | <10 | >500 | >500 | >500 | >500 | >500 | >500 | >500 | 25 |
|  | pH 8.2 | 100 | >500 | >500 | >500 | >500 | >500 | >500 | >500 | 100 |
| (XXVII) | pH 6.8 | 25 | >500 | 500 | 500 | 500 | >500 | 500 | 250 | <10 |
|  | pH 8.2 | 50 | >500 | >500 | >500 | >500 | >500 | >500 | 250 | 50 |
| (XXVIII) | pH 6.8 | <10 | >500 | >500 | >500 | 500 | >500 | >500 | >500 | <10 |
|  | pH 8.2 | 50 | >500 | >500 | >500 | >500 | >500 | >500 | >500 | 50 |

TABLE III

Minimum Inhibitory Concentrations for Test
Compounds in Yeast/Fungi Species (in ppm)

| COMPOUND EXAMPLE NO. | An | Ca | Pc | Sc | Tv | Ap | Fo |
|---|---|---|---|---|---|---|---|
| STANDARD | >500 | >500 | >500 | 500 | >500 | >500 | >500 |
| I | 25 | <10 | 25 | <10 | 500 | <10 | 250 |
| II | 2.5 | 5 | .55 | 2.5 | 5 | 2.5 | 5 |
| III | 25 | 50 | 25 | 25 | 50 | <10 | 25 |
| VI | <10 | 25 | 25 | 25 | 250 | <10 | 100 |
| V | 25 | 25 | 25 | 25 | 50 | 25 | 25 |
| VI | 500 | 250 | 500 | >500 | >500 | 250 | >500 |
| VII | 5 | 5 | 5 | 5 | 10 | 2.5 | 10 |
| VIII | 25 | <10 | 50 | 15 | 500 | <10 | 100 |
| IX | 250 | 500 | >500 | 250 | >500 | 250 | >500 |
| X | 100 | 500 | >500 | >500 | >500 | 25 | >500 |
| XI | 25 | 250 | >500 | 500 | >500 | 25 | >500 |
| XII | 500 | >500 | >500 | >500 | >500 | 250 | >500 |
| XIII | >500 | >500 | >500 | >500 | >500 | >500 | >500 |
| XIV | >500 | >500 | >500 | >500 | >500 | >500 | >500 |
| XV | >500 | >500 | >500 | >500 | >500 | >500 | >500 |
| XVI | >500 | >500 | >500 | >500 | >500 | >500 | >500 |
| XVII | >500 | >500 | >500 | >500 | >500 | >500 | >500 |
| XVIII | <10 | 25 | <10 | <10 | 25 | <10 | <10 |
| XIX | 250 | >500 | >500 | >500 | >500 | 500 | >500 |
| XX | <10 | <10 | <10 | <10 | 25 | <10 | 25 |
| XXI | 5 | 10 | 10 | 5 | 25 | 2.5 | 25 |
| XXII | <10 | <10 | <10 | <10 | 50 | <10 | 25 |
| XXIII | 5 | 25 | 10 | 10 | 50 | 5 | 25 |
| XXIV | <10 | <10 | <10 | <10 | <10 | <10 | <10 |
| XXV | 25 | 100 | 25 | 250 | 500 | 25 | 500 |
| XXVI | <10 | <10 | <10 | <10 | 250 | <10 | 500 |
| XXVII | 500 | 500 | 500 | 500 | 500 | 500 | 500 |
| XXVIII | <10 | <10 | <10 | 25 | 100 | <10 | 50 |

Marine Antifouling Activity

The present invention is also directed to a method for inhibiting marine organisms. The term "marine organisms" is meant to include marine animals, such as barnacles, serpulid, bryozoa, oysters and hydroids, and marine plants, such as green algae and brown algae. The method for inhibiting marine organisms comprises contacting a surface exposed to a marine environment in which marine organisms grow with a marine antifouling effective amount of the compound of this invention.

As appreciated by those skilled in the art, not all of the compounds disclosed herein are active at the same concentrations or against the same marine organism species. That is, there may be some compound-to-compound variation in marine antifouling potency and spectrum of marine antifouling activity. Furthermore, the level of a specific compound's marine antifouling activity may be dependent on various factors including the specific materials with which the compound is formulated.

As used herein, the term "marine antifouling effective amount" refers to that amount of one or a mixture of two or more of the compounds of this invention needed to exhibit inhibition of selected marine organisms. Typically, this amount varies from providing about 1 weight percent to about 30 weight percent of the compound to a marine antifouling composition which is used to treat a surface exposed to a marine environment in which marine organisms live or grow. Such amounts vary depending upon the particular compound tested and marine organism to be treated. Also, the exact concentration of the compounds to be added in the preparation of industrial and consumer formulations may vary within a product type depending upon the components of the formulation.

A composition comprising a marine antifouling effective amount of the compound will also comprise an inert diluent which may bet for example, in the form of a paint. Particularly preferred are those paints having a vinyl resin binder such as, for example, a plasticized polyvinyl chloride or a polyvinyl chloride-polyvinyl acetate type. Preferably, the binders are formulated as latexes or emulsions. In a paint composition, the compound of the present invention is preferably used in an amount from about 1 to about 30 weight percent and, most preferably, from about 10 to about 25 weight percent. In addition to vinyl resin binder paints, epoxy and polyurethane binder paints containing the compound may also be useful. Coatings and films prepared from paints comprising the compound of the present invention typically remain substantially free from build-up of marine organisms for periods ranging from about 3 to about 12 months, depending upon the concentration of the compound and the thickness of the applied coating or film.

The term "a surface exposed to a marine environment" refers to a surface where a marine organism naturally or normally lives or grows. Typically, such a surface will be an area that is in continual or periodic contact with a marine environment such as an ocean or other body of water. Typical surfaces include, for example, a ship hull.

The marine antifouling activity of the compounds of the present invention is demonstrated by the following techniques.

Test panels are prepared from clear, rigid polyvinyl chloride film that is 0.381×10-3 m thick and has one textured surface. The test panels are 0.1524 m by 0.1524 m squares that have 0.00635 m holes punched at corners on 0.127 m centers. A 0.102 square template, with a 0.067 m diameter hole at the center, is attached to the center of the textured surface of the test panels.

A candidate marine antifoulant compound (1.0 g) is stirred into a resinous latex binder (9.0 g). A portion of the compound/binder mixture (1.5 g) is added to the center of the test panel and uniformly spread over the circular area inside the template.

Water is added dropwise as needed to properly spread the compound/binder mixture. The template prevents the compound/binder mixture from spreading beyond the uncovered area. The test panel is allowed to sit for between 10 to 30 minutes until the edge of the spread compound/binder mixture has dried. The template is then removed. The test panel is then allowed to dry for 8 to 12 hours at room temperature.

Two test panels are prepared for each candidate marine antifoulant compound. Two control test panels are also prepared by only treating with the resinous latex binder. One test panel of each candidate marine surfactant compound is attached over a white background to the topside of an exposure support apparatus. The second test panel is attached over a black background to the underside of the exposure support apparatus. The exposure support apparatus is placed horizontally 0.0254 m under a marine surface with the white background topside facing up. The exposure support apparatus is exposed to the marine environment for both 6 and 10 weeks during which time the control test panels become substantially covered with mature marine organism growth on both the topside and underside exposures.

After being removed from the exposure support apparatus, each test panel is inspected and rated for marine organism growth on both the treated and untreated areas of the test panel. The marine organisms present on the treated and untreated areas are noted. The presence of algae spores and bacterial slime are noted but not included in rating each test panel. The test panels are rated on a scale from 10 (representing completely free of marine organism growth) to 0 (representing completely covered with marine organism growth).

In Table IV, the marine antifouling rating values for some of the active compounds of the present invention are set forth, as well as the ratings for control panels (with no marine antifouling compound and referred to as "Control").

In addition, test panels were prepared using tributyl tin oxide, a known marine antifouling compound. One set of such panels used the tributyl tin oxide in a commercially available ship-hull paint (referred to in Table IV as "STANDARD II") which was employed in the same manner as the resinous latex binder used on the other test panels. A second set of such panels used the tributyl tin oxide at a 10 percent concentration in the resinous latex binder (referred to in Table IV as "STANDARD III").

TABLE IV

Marine Antifouling Rating for Test Compounds

| | Marine Antifouling Ratings | | | |
|---|---|---|---|---|
| | 6 Week Test | | 10 Week Test | |
| Compound (Example No.) | Top Panel | Bottom Panel | Top Panel | Bottom Panel |
| II | 9 | 3 | 2 | 2 |
| Control | 1 | 1 | 3 | 1 |
| STANDARD II | 10 | 10 | 10 | 10 |
| STANDARD III | 10 | 10 | 9 | 10 |

What is claimed is:

1. A 4,5-dimercapto-1,3-dithiolo-2-one (or thione) maleimide compound corresponding to the formula

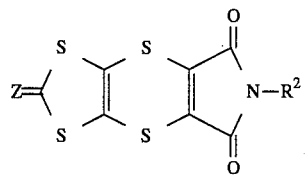

wherein $R^2$ represents $C_3$–$C_{10}$ cycloalkyl, $C_1$–$C_{10}$ straight or branched chain alkoxy, $C_3$–$C_{10}$ cycloalkoxy, an ester of the formula —$CH_2CH_2O$—$C(O)$—$R^1$, wherein $R^1$ represents $C_1$–$C_5$ straight or branched chain alkyl or $C_3$–$C_5$ cycloalkyl and Z represents oxygen or sulfur.

2. The compound as defined in claim 1 which is 6-cyclohexyl-2-oxo-5H-1,3-dithiolo-(5,6) (1,4)-dithiino(2,3-C)pyrrole-5,7(6H)-dione.

3. The compound as defined in claim 1 which is 6-(2-(acetyloxy)ethyl)-2-thioxo-5H-1,3-dithiolo-(5,6)(1,4)-dithiino(2,3-C)pyrrole-5,7(6H)-dione.

4. An antimicrobial composition comprising an inert diluent and an antimicrobially-effective amount of 6-(2-(acetyloxy)ethyl)-2-thioxo-5H-1,3-dithiolo-(5,6)(1,4)-dithiino(2,3-C)pyrrole-5,7(6H)-dione.

5. An antimicrobial composition comprising an inert diluent and an antimicrobially-effective amount of 6-cyclohexyl-2-oxo-5H- 1,3-dithiolo-(5,6) (1,4)dithiino-(2,3-C)pyrrole-5,7(6H)-dione.

6. A method for inhibiting microorganisms in a microbial habitat comprising contacting said microbial habitat with an antimicrobially-effective amount of a 4,5-dimercapato-1,3-dithiolo-2-one (or thione) maleimide compound corresponding to the formula

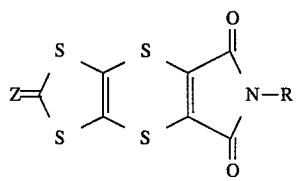

wherein R represents —H, phenyl, benzyl, phenethyl, a $C_1$–$C_{10}$ straight or branched chain alkyl radical, a $C_3$–$C_{10}$ cycloalkyl radical, a $C_1$–$C_{10}$ straight or branched chain alkoxy radical, a $C_3$–$C_{10}$ cycloalkoxy, an ester of the formula —$CH_2CH_2O$—$C(O)$—$R^1$, wherein $R^1$ represents a $C_1$–$C_5$ straight or branched chain alkyl radical or a $C_3$–$C_5$ cycloalkyl radical and Z represents oxygen or sulfur.

7. The method as defined in claim 6 wherein the compound is 2-thioxo-5H-1,3-dithiolo-(5,6) (1,4)-dithiino(2,3-C)pyrrole-5,7(6H)-dione.

8. The method as defined in claim 6 wherein the compound is 6-methyl-2-thioxo-5H-1,3-dithiolo- (5,6)(1,4)dithiino(2,3-C)pyrrole-5,7(6H)-dione.

9. The method as defined in claim 6 wherein the compound is 6-ethyl-2-thioxo-5H-1,3-dithiolo- -(5,6)(1,4)dithiino(2,3-C)pyrrole-5,7(6H)-dione.

10. The method as defined in claim 6 wherein the compound is 6-n-propyl-2-thioxo-5H-1,3-dithiolo-(5,6)(1,4)dithiino(2,3-C)pyrrole-5,7(6H)-dione.

11. The method as defined in claim 6 wherein the compound is 6-(1-methylethyl)-2-thioxo-5H-1,3- -dithiolo-(5,6)(1,4)dithiino(2,3-C)pyrrole-5,7(6H)- -dione.

12. The method as defined in claim 6 wherein the compound is 6-n-butyl-2-thioxo-5H-1,3-dithiolo- -(5,6)(1,4)dithiino(2,3-C)pyrrole-5,7(6H)-dione.

13. The method as defined in claim 6 wherein the compound is 6-(2-(acetyloxy)ethyl)-2-thioxo-5H-1,3-dithiolo-(5,6)(1,4)-dithiino(2,3-C)pyrrole-5,7(6H)-dione.

14. The method as defined in claim 6 wherein the compound is 2-oxo-5H-1,3-dithiolo-(5,6)(1,4)-dithiino-(2,3-C)pyrrole-5,7-(6H)-dione.

15. The method as defined in claim 6 wherein the compound is 6-ethyl-2-oxo-5H-1,3-dithiolo-(5,6)(1,4)dithiino (2,3-C)pyrrole-5,7(6H)-dione.

16. The method as defined in claim 6 wherein the compound is 6-(1-methylethyl )-2-oxo-5H-1,3-dithiolo-(5,6)(1,4)dithiino(2,3-C)pyrrole-5,7(6H)- -dione.

17. The method as defined in claim 6 wherein the compound is 6-n-butyl-2-oxo-5H-1,3-dithiolo- -(5,6) (1,4)dithiino(2,3-C)pyrrole-5,7(6H)-dione.

18. The method as defined in claim 6 wherein the compound is 6-(1-methylpropyl)-2-oxo-5H-1,3-dithiolo-(5,6)(1,4)dithiino(2,3-C)pyrrole-5,7(6H)-dione.

19. The method as defined in claim 6 wherein the compound is 6-n-hexyl-2-oxo-5H-1,3-dithiolo-(5,6)(1,4)dithiino(2,3-C)pyrrole-5,7(6H)-dione.

20. The method as defined in claim 6 wherein the compound is 6-cyclohexyl-2-oxo-5H-1,3-dithiolo- -(5,6)(1,4)dithiino(2,3-C)pyrrole-5,7(6H)-dione.

21. The method as defined in claim 6 wherein the compound is 6-benzyl-2-oxo-5H-1,3-dithiolo-(5,6)(1,4)dithiino(2,3-C)pyrrole-5,7(6H)-dione.

22. The method of claim 6 wherein the compound is present in the composition in an amount to provide from about 1 part per million to about 5,000 parts per million by weight of the compound to the microbial habitat.

23. A method for preventing the growth of marine organisms on a surface exposed to a marine environment in which marine organisms grow comprising contacting said surface with a marine antifouling effective amount of a 4,5-dimercapto-1,3-dithiolo-2-one or thione maleimide compound corresponding to the formula

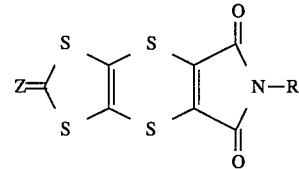

wherein R represents —H, phenyl, benzyl, phenethyl, a $C_1$–$C_{10}$ straight or branched chain alkyl radical, a $C_3$–$C_{10}$ cycloalkyl radical, a $C_1$–$C_{10}$ straight or branched chain alkoxy radical, a $C_3$–$C_{10}$ cycloalkoxy, an ester of the formula —$CH_2CH_2O$—$C(O)$—$R^1$, wherein $R^1$ represents a $C_1$–$C_5$ straight or branched chain alkyl radical or a $C_3$–$C_5$ cycloalkyl radical and Z represents oxygen or sulfur.

24. The method of claim 23 wherein the compound is contacted with the surface in an amount from about 1 to about 30 weight percent of a composition comprising an inert diluent in admixture with the compound.

* * * * *